United States Patent
Narahara et al.

(10) Patent No.: US 8,865,403 B2
(45) Date of Patent: Oct. 21, 2014

(54) NUCLEIC ACID ANALYZING DEVICE AND NUCLEIC ACID ANALYZER

(75) Inventors: Masatoshi Narahara, Hitachinaka (JP); Toshiro Saito, Hitachinaka (JP); Naoshi Itabashi, Kokubunji (JP); Jiro Yamamoto, Kokubunji (JP); Hiroyuki Uchiyama, Kokubunji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 451 days.

(21) Appl. No.: 12/997,469

(22) PCT Filed: May 13, 2009

(86) PCT No.: PCT/JP2009/058885
§ 371 (c)(1),
(2), (4) Date: Dec. 10, 2010

(87) PCT Pub. No.: WO2009/150916
PCT Pub. Date: Dec. 17, 2009

(65) Prior Publication Data
US 2011/0081655 A1 Apr. 7, 2011

(30) Foreign Application Priority Data
Jun. 13, 2008 (JP) .................................. 2008-154798

(51) Int. Cl.
*C12Q 1/68* (2006.01)
*C12M 1/36* (2006.01)
*G01N 21/00* (2006.01)
*G01N 21/64* (2006.01)

(52) U.S. Cl.
CPC .................................... *G01N 21/648* (2013.01)
USPC ...... 435/6.1; 435/91.1; 435/287.2; 422/82.07

(58) Field of Classification Search
None
See application file for complete search history.

(56) References Cited

U.S. PATENT DOCUMENTS

| 6,017,696 | A | 1/2000 | Heller |
| 7,864,313 | B2 * | 1/2011 | Baumberg et al. ............ 356/301 |

(Continued)

FOREIGN PATENT DOCUMENTS

| JP | 2007-078451 | 3/2007 |
| JP | 2007-240361 | 9/2007 |

OTHER PUBLICATIONS

Braslavsky, I., et al., "Sequence information can be obtained from single DNA molecules", PNAS, Apr. 1, 2003, pp. 3960-3964, vol. 100 No. 7.

(Continued)

*Primary Examiner* — Betty Forman
(74) *Attorney, Agent, or Firm* — McDermott Will & Emery LLP (57) ABSTRACT

An object of the present invention relates to distinguishing, from a fluorophore of an unreacted substrate, a single fluorophore attached to a nucleotide that is incorporated into a probe by a nucleic acid synthesis. The present invention relates to a nucleic acid analyzing device that analyzes a nucleic acid in sample by fluorescence, wherein a localized surface plasmon is generated by illumination, and a probe for analyzing the nucleic acid in the sample is on the site where the surface plasmon is generated. According to the present invention, since it is possible to efficiently produce fluorescence intensifying effects due to the surface plasmon and to immobilize the probe to a region within the reach of the fluorescence intensifying effects, it becomes possible to measure a nucleic acid synthesis without removing unreacted nucleotide to which fluorophores are attached.

9 Claims, 6 Drawing Sheets

(56) References Cited

U.S. PATENT DOCUMENTS

| | | | |
|---|---|---|---|
| 2002/0044893 A1* | 4/2002 | Corn et al. | 422/68.1 |
| 2004/0029152 A1 | 2/2004 | Ishida | |
| 2005/0084912 A1* | 4/2005 | Poponin | 435/7.1 |
| 2006/0273245 A1 | 12/2006 | Kim et al. | |
| 2008/0014630 A1 | 1/2008 | Furuki | |
| 2008/0032301 A1* | 2/2008 | Rank et al. | 435/6 |
| 2008/0218761 A1 | 9/2008 | Nishikawa et al. | |
| 2009/0140128 A1* | 6/2009 | Oldham et al. | 250/216 |

OTHER PUBLICATIONS

Anger, P., et al., "Enhancement and Quenching of Single-Molecule Fluorescence", Physical Review Letters, Mar. 2006. pp. 113002-1-113002-4, vol. 96, The American Physical Society.

Fu, Y., et al., "Enhanced Fluorescence of Cy5-Labeled DNA Tethered to Silver Island Films: Fluorescence Images and Time-Resolved Studies Using Single-Molecule Spectroscopy", Analytical Chemistry, Sep. 2006, pp. 6238-6245, vol. 78 No. 17, American Chemical Society.

Bharadwaj, P., et al., "Nanoplasmonic enhancement of single-molecule fluorescence", Nanotechnology, 2007, vol. 18, IOP Publishing Ltd.

Fromm, D., et al., "Gap-Dependent Optical Coupling of Single "Bowtie" Nanoantennas Resonant in the Visible", Nano Letters, 2004, pp. 957-961, vol. 4 No. 5.

Ju, J., et al., "Four-color DNA Sequencing by synthesis using cleavable fluorescent nucleotide reversible terminators", PNAS, Dec. 2006, pp. 19635-19640, vol. 103 No. 52.

Korlach, J., et al., "Selective aluminum passivation for targeted immobilization of single DNA polymerase molecules in zero-mode waveguide nanostructures", PNAS, Jan. 2008, pp. 1176-1181, vol. 105 No. 4.

* cited by examiner

NUCLEIC ACID ANALYZING DEVICE AND NUCLEIC ACID ANALYZER

RELATED APPLICATIONS

This application is the U.S. National Phase under 35 U.S.C. §371 of International Application No. PCT/JP2009/058885, filed on May 13, 2009, which in turn claims the benefit of Japanese Application No. 2008-154798, filed on Jun. 13, 2008, the disclosures of which Applications are incorporated by reference herein.

TECHNICAL FIELD

The present invention relates to nucleic acid analyzing devices and nucleic acid analyzers.

BACKGROUND ART

For nucleic acid analyzing devices, new techniques for sequencing DNA and RNA are being developed.

With methods in common use today that employ electrophoresis, a cDNA fragment sample synthesized in advance through reverse transcription reaction of a DNA fragment or RNA sample for sequencing is prepared, electrophoresis is performed after performing a dideoxy reaction by the well-known Sanger method, and a molecular weight separation/expansion pattern is measured and analyzed.

In contrast, as presented in Non-Patent Document 1, there has recently been proposed a method for sequencing DNA or the like by immobilizing it on a substrate. In this method, a sample DNA fragment to be analyzed is randomly captured on the surface of the substrate one molecule at a time and extended by one base at a time, and the result thereof is detected by fluorescence microscopy, thereby determining the base sequence. Specifically, there is first performed a step in which a DNA polymerase reaction is caused using four kinds of dNTP derivatives (MdNTP) which, by being incorporated into a template DNA as substrates of DNA polymerases, are capable of terminating DNA strand nucleic acid synthesis by the presence of a protective group, and which have detectable labels. A step of detecting the incorporated MdNTP by way of fluorescence, etc., and a step of returning the MdNTP to an extendible state are subsequently performed. With these three steps as one cycle, the sample DNA is sequenced by repeating this cycle. With this technique, since DNA fragments can be sequenced one molecule at a time, it is possible to analyze a large number of fragments simultaneously, and analysis throughput can thus be increased. Further, with this scheme, since it is possible to sequence single DNA molecules, there is a possibility that sample DNA purification and amplification in cloning, PCR, etc., which had been problematic in conventional techniques, may be rendered unnecessary, and faster genome analysis and genetic testing could be expected.

PRIOR ART DOCUMENTS

Patent Documents

Patent Document 1: JP Patent Publication (Kohyo) No. 2007-501391 A
Patent Document 2: JP Patent Publication (Kokai) No. 2002-214142 A
Patent Document 3: JP Patent Publication (Kokai) No. 2007-240361 A
Patent Document 4: JP Patent Publication (Kokai) No. 2008-20412 A
Patent Document 5: US Patent No. 6,017,696

Non-Patent Documents

Non-Patent Document 1: P.N.A.S. 2003, vol. 100, pp. 3960-3964
Non-Patent Document 2: Physical Review Letters 2006, 96, pp. 113002-113005
Non-Patent Document 3: Anal. Chem. vol. 78, 6238-6245
Non-Patent Document 4: Nanotechnology, 2007, vol. 18, pp. 44017-44021
Non-Patent Document 5: Nano Letters, 2004, vol. 4, 957-961
Non-Patent Document 6: P.N.A.S. 2006, vol. 103, pp. 19635-19640
Non-Patent Document 7: P.N.A.S. 2008, vol. 105, pp. 1176-1181

SUMMARY OF THE INVENTION

Problems to be Solved by the Invention

For the analysis of a base sequence using nucleic acid synthesis on a substrate, those of a successive reaction scheme, so to speak, are popular, where, as represented by the scheme disclosed in Non-Patent Document 1, the washing and measuring of single base extension reacted and unreacted nucleotide are taken to be one cycle. When sequencing single DNA molecules, the fluorescence of a single fluorophore attached to a nucleotide incorporated into double-stranded DNA by a single base extension reaction on a probe DNA is measured. However, in ordinary fluorescence measurement, a fluorophore captured on a probe DNA cannot be distinguished from a fluorophore attached to an unreacted nucleotide floating in the vicinity thereof. Thus, it was necessary to wash unreacted nucleotide for each single base extension. Due to the inclusion of this washing step, there were such problems as the fact that it is necessary to form complex passages, a solution delivering device, and a waste liquid treating device on the substrate, the fact that large quantities of reaction reagents are consumed, and, further, the fact that the total reaction time required for analysis becomes longer.

In order to distinguish a single fluorophore captured on a probe DNA from a fluorophore of an unreacted substrate, there must be created a condition in which the fluorescence intensity from the fluorophore captured on the probe DNA is greater and the intensity from the floating fluorophore lesser.

An object of the present invention relates to distinguishing a single fluorophore attached to a nucleotide incorporated into double-stranded DNA by a nucleic acid synthesis from a fluorophore of an unreacted substrate.

Means for Solving the Problems

As such, through extensive consideration, the present inventors have found a method of distinguishing a fluorophore attached to a nucleotide incorporated into double-stranded DNA by a nucleic acid synthesis from a floating fluorophore by disposing a measuring probe within a fluorescence intensifying field caused by a localized surface plasmon generated between a plurality of opposing metal structures. In particular, the present inventors have given extensive consideration to the shape of a metal structure that creates a strong fluorescence intensifying field as well as to a method for immobilizing a measuring probe within the localized intensifying field, and have found a method capable of simultaneously attaining both of the above.

The present invention relates to a nucleic acid analyzing device that analyzes a nucleic acid in a sample through fluorescence measurement, wherein a localized surface plasmon is generated through illumination, and a probe for measuring the nucleic acid in the sample is located at the site where the surface plasmon is generated.

Effects of the Invention

According to the present invention, it is possible to efficiently produce a fluorescence intensifying effect caused by a localized surface plasmon and to immobilize a measuring probe on a region within the reach of the fluorescence intensifying effect. Consequently, it becomes possible to measure base nucleic acid synthesis without removing unreacted nucleotide to which fluorophores are attached.

MODE FOR CARRYING OUT THE INVENTION

In an embodiment of the present invention, there is disclosed a nucleic acid analyzing device that analyzes a nucleic acid in a sample by luminescence, the nucleic acid analyzing device comprising a substrate; wherein a plurality of metal structures face each other on the substrate, a localized surface plasmon is generated by in a space where the metal structures face each other by illumination, a second metal is under the space, whose material is different from that of the metal structures, and a probe for analyzing the nucleic acid in the sample is on the second metal. Using the difference in reactivity between the metal that forms the metal structures and the second metal, it is possible to specifically dispose the measuring probe on the second metal.

In another embodiment of the present invention, there is disclosed a nucleic acid analyzing device that analyzes a nucleic acid in a sample by luminescence, the nucleic acid analyzing device comprising a substrate, wherein a plurality of metal structures face each other on the substrate, a localized surface plasmon is generated in a space where the metal structures face each other by illumination metal structures, an insulator is under the space, and a probe for analyzing the nucleic acid in the sample. Using the difference in reactivity between the metal that forms the metal structures and the insulator, it is possible to specifically dispose the measuring probe on the insulator.

In a further embodiment of the present invention, there is disclosed a nucleic acid analyzing device wherein the above-mentioned luminescence is fluorescence. By combining optical filters of a detection device, it is possible to simultaneously detect fluorescence of two or more colors.

In a further embodiment of the present invention, there is disclosed a nucleic acid analyzing device wherein the above-mentioned probe is one or more macromolecules selected from a nucleic acid and a protein. Nucleic acids or proteins such as nucleic acid synthetases, etc., have high specificity in incorporating target nucleic acids, and it is thus possible to specifically measure only the target.

In a further embodiment of the present invention, there is disclosed a nucleic acid analyzing device wherein the metal structures comprise one or more kinds of metals selected from gold, silver, platinum, aluminum and copper. These metals are capable of enhancing the intensifying effect caused by the localized surface plasmon.

In a further embodiment of the present invention, there is disclosed a nucleic acid analyzing device wherein the plurality of metal structures facing each other are arrayed on the substrate. Since only some arbitrarily chosen reaction site(s) on the substrate need be analyzed, it is possible to simplify the configuration of the analyzer.

In a further embodiment of the present invention, there is disclosed a nucleic acid analyzing device wherein the gap between the plurality of metal structures is 15 nm or less. By making the gap between the metal structures be small, it is possible to enhance the intensifying effect caused by the localized plasmon. In addition, it is possible to reduce the size of the measuring probe immobilization region, and the proportion of grids where only a single molecule is immobilized can be increased.

In a further embodiment of the present invention, there is disclosed a nucleic acid analyzing device wherein the probe is a single molecule. Since an amplification step for the target nucleic acid is unnecessary, it is possible to reduce analysis time.

In a further embodiment of the present invention, there is disclosed a nucleic acid analyzer comprising: a device that supplies to a nucleic acid analyzing device one or more kinds of biomolecules comprising a nucleotide, a nucleotide comprising a fluorophore, a nucleic acid synthetase, a primer, and a nucleic acid sample; a device that illuminates the nucleic acid analyzing device; and a fluorescence detection device that measures the fluorescence of a fluorophore that is incorporated into a nucleic acid strand due to a nucleic acid synthesis that occurs by way of the coexistence of, on the nucleic acid analyzing device, the one or more kinds of biomolecules comprising the nucleotide, the nucleotide comprising the fluorophore, the nucleic acid synthetase, the primer, and the nucleic acid sample, wherein base sequence information of the nucleic acid sample-is obtained. Due to the intensifying effect of the localized surface plasmon, expensive optical members that are required for high-sensitivity detection become unnecessary.

In a further embodiment of the present invention, there is disclosed a method for sequencing a nucleic acid sample, the method comprising: supplying to the above-mentioned nucleic acid analyzing device one or more kinds of biomolecules comprising a nucleotide comprising a fluorophore, a nucleic acid synthetase, a primer and a nucleic acid sample; illuminating the nucleic acid analyzing device; generating a localized surface plasmon in the space where the metal structures face each other; and measuring the fluorescence of a fluorophore that is incorporated into a nucleic acid strand due to a nucleic acid extension reaction that occurs by way of the coexistence of the nucleotide, the nucleic acid synthetase, and the nucleic acid sample.

Novel features and effects of the present invention mentioned above and otherwise are described below with reference to the drawings.

Although specific embodiments are described herein in detail for a complete understanding of the present invention, the present invention is by no means limited to the content disclosed herein.

Embodiment 1

Figure 1:
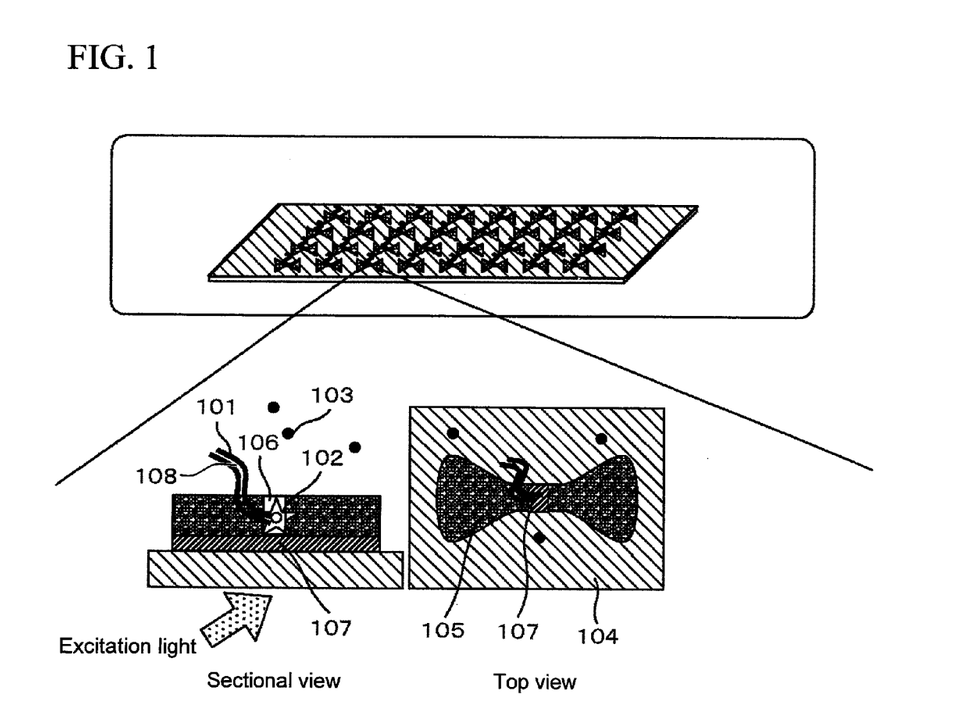
FIG. 1 is a schematic view of a nucleic acid analyzing device according to an embodiment of the present invention.

A device according to an embodiment of the present invention is described with reference to FIG. 1. In order to distinguish a fluorophore 102 captured on a probe 101 from a fluorophore 103 of an unreacted substrate, it is necessary to either differentiate the intensity of the light which illuminates the fluorophore 102 captured on the probe 101 from that which illuminates the floating unreacted fluorophore 103, or arrange for an irradiation process for only the fluorophore 102 on the probe 101 to take place efficiently. The present embodiment of the invention is based on the latter idea and is based on a physical phenomenon where, as reported in Physical Review Letters 2006, 96, pp. 113002-113005 (Non-Patent Document 2), a localized surface plasmon increases both the probabilities of electronic transition due to light absorption by a molecule and of radiative transition from the excited singlet state to the ground state. A fluorescence intensifying effect of the localized surface plasmon on the order of several times to several tens of times may be expected. The range over which the influence thereof has reach varies with the structure and shape of metal structures 105 on a substrate 104. In a case where triangle column-like structures face each other as presented in the present embodiment of the invention, the fluorescence intensifying field caused by the localized surface plasmon is space 106.

Thus, in the present embodiment of the invention, only the fluorophore 102 incorporated into the probe 101 reaps the benefit of fluorescence intensification, producing a difference in fluorescence intensity of or more than several times to several tens of times that of the floating fluorophore 103.

With respect to the phenomena of fluorescence intensification by surface plasmons, there are known those that employ silver island structures on the order of nanometers as reported in Anal. Chem. vol. 78, 6238-6245 (Non-Patent Document 3), and those that employ gold spherical nanoparticles with a diameter of several tens of nanometers as reported in Nanotechnology, 2007, vol. 18, pp. 44017-44021 (Non-Patent Document 4). However, it is virtually impossible to dispose, for each of the probes, several tens of thousands to several hundreds of thousands of island-structured pads or spherical nanoparticles on a flat and smooth substrate such as a glass substrate, etc. In particular, it is impossible to immobilize probes at predetermined locations. As such, the present inventors gave extensive consideration to a structure that would be capable of generating a strong localized surface plasmon and of immobilizing the probe 101 in the space 106 in the vicinity of the site where the localized surface plasmon is generated. Further, in view of production costs, it was considered desirable that the structure be producible using thin film processes that are employed in the production of semiconductors and circuit boards, and a structure was thus considered.

The fact that when triangle columns are in close proximity a strong localized surface plasmon is generated in the space therebetween is disclosed in Nano Letters, 2004, vol. 4, 957-961 (Non-Patent Document 5). A stronger localized surface plasmon can be generated the closer the distance between the triangle columns is. However, with this metal body structure, it is not possible to specifically dispose the measuring probe in the space where the localized surface plasmon is generated. Through extensive consideration, the present inventors have invented a structure in which a second metal 107 that is different from the metal that forms the triangle columns is disposed between the space 106 in which the localized surface plasmon is generated and the substrate 104, thereby immobilizing the probe 101 to the second metal 107.

For the metal structures 105 capable of generating the localized surface plasmon, gold, silver, platinum, aluminum, copper, etc., are known. There are no particular limitations with respect to the second metal 107 as long as it allows for specific immobilization of the probe 101 using the difference in chemical properties in relation to the surface of the metal structures 105. In addition, the desired probe 101 may also be immobilized by selecting a suitable functional group and imparting it to the second metal, or by causing a reaction between a functional group within the probe 101 and the above-mentioned functional group or a further modified functional group with the above as the reaction origin. As combinations of such metal structures 105 and second metal 107, if the metal structures 105 are noble metals such as gold, silver, platinum, etc., then the second metal 107 may be at least one kind of metal selected from titanium, nickel, chromium, iron, cobalt, cadmium, aluminum, gallium, indium, zirconia, niobium, hafnium, and tantalum, or an alloy thereof. Alternatively, an electrically conductive oxide film such as ITO, etc., may be used. By causing carboxylic acid, phosphonic acid, phosphoric ester, or an organosilane compound to react on an oxide-film formed on the surface of the second metal 107, it is possible to introduce a desired functional group for immobilizing the probe 101. If the metal structures 105 are aluminum, copper, etc., the second metal may be at least one kind of metal selected from gold, silver, mercury, indium, palladium, ruthenium, and zinc, or an alloy thereof. By causing an organosulfur compound, an organoselenium compound, an organotellurium compound, etc., to react with the surface of the second metal, it is possible to introduce a desired functional group for immobilizing the probe 101.

Next, a structure in which an insulator is present between the space 106 and the substrate 104 of the present embodiment of the invention will be described. Although there are no particular limitations with respect to the insulator to be used, from the perspective of workability of nanoregions, a material with which a thin film can be formed through vapor deposition, sputtering, CVD (Chemical Vapor Deposition), PVD (Physical Vapor Deposition), etc., is preferable. Examples of such a material might include carbides, nitrides, borides, silicides, oxides, etc., of silicon, titanium, beryllium, zirconium, tungsten, boron, hafnium, vanadium, tantalum, aluminum, thorium, molybdenum, iron, etc.

Although there are no particular limitations with respect to the functional group to be introduced on the second metal 107 or the insulator either, examples of a reaction origin for immobilizing the probe 101 may include amino groups, thiol groups, carboxyl groups, hydroxyl groups, aldehyde groups, ketone groups, etc. Further, as a method of improving the reaction efficiency for immobilizing the probe 101, a functional group such as an NHS-ester group, an imide ester group, a sulfhydryl group, an epoxy group, a hydrazide group, etc., may be introduced using a bifunctional compound. In addition, in order to improve the rate at which single molecules are immobilized within the intensifying field, the probe 101 may be immobilized by way of a bulky compound such as avidin, dendron, crown ether, etc.

There are no particular limitations with respect to the probe 101 either, as long as it is capable of capturing a target nucleic acid 108. Examples of a probe capable of directly capturing the nucleic acid 108 may include nucleic acids such as DNA, RNA, PNA, etc., or proteins such as enzymes, etc. The nucleic acid 108 may also be captured by way of chromosomes, nucleoids, cell membranes, cell walls, viruses, antigens, antibodies, lectins, haptens, receptors, peptides, sphingo sugar, sphingolipid, etc.

Figure 2:
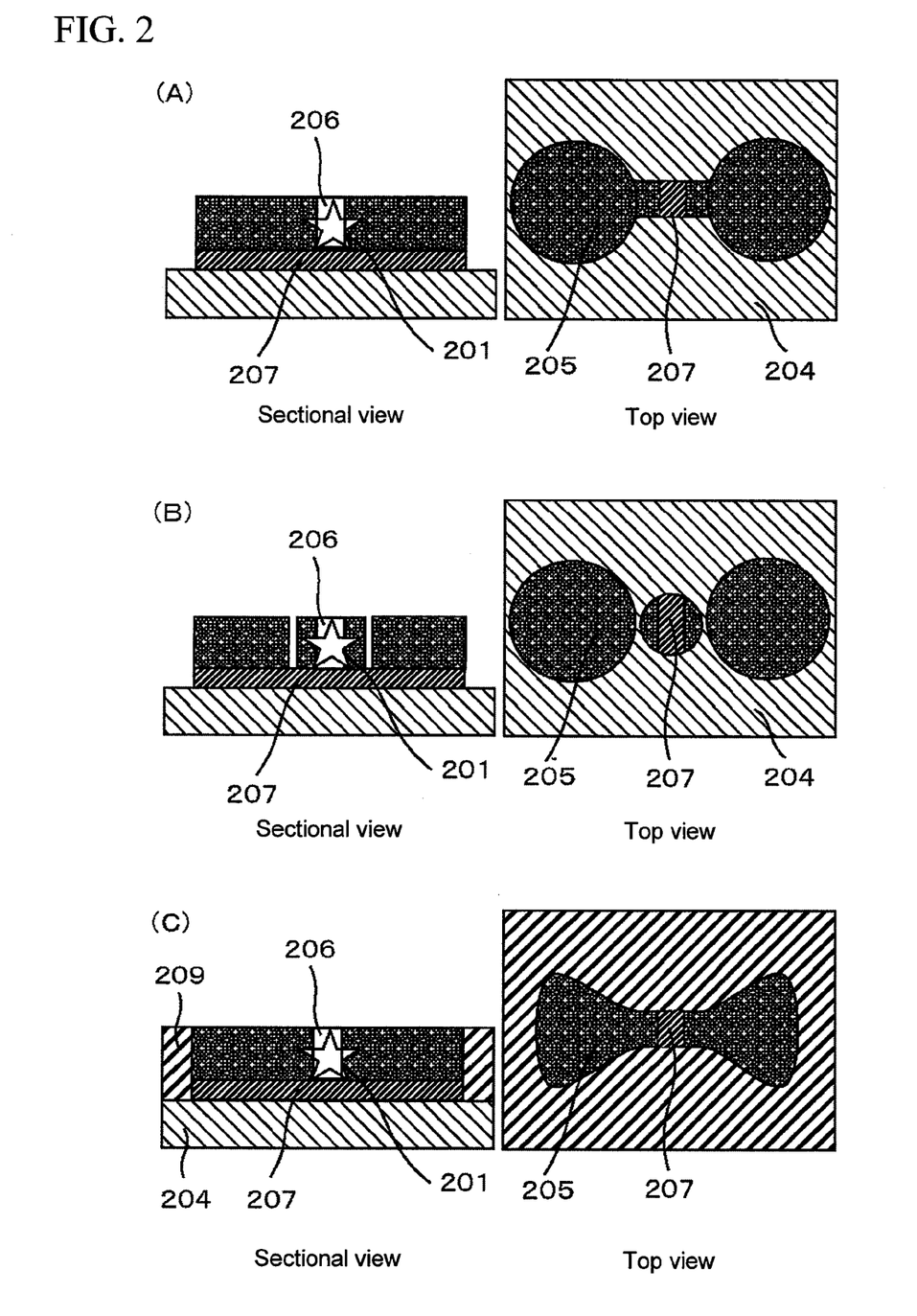
FIG. 2 is a schematic view of a nucleic acid analyzing device according to an embodiment of the present invention.

The appropriate shape and size for the metal structures 105 vary with the wavelength of the light with which they are illuminated. Specifically, the resonant frequency suited for the generation of surface plasmons is based on the interaction between the group of free electrons on the surface of the metal structure and light. When visible light is employed as the excitation light, approximately 10 to 1,000 nm would be suitable for both the width and height with respect to the size of the metal structure. However, these conditions are by no means binding. There may also be, for example, those in which, as shown in FIG. 2(A), circular columns are linked with a rectangular column and a space 206, where the localized surface plasmon is to be generated, is provided in the middle of the square column, those in which, as shown in (B), circular columns are arranged in a row, and the space 206 is provided within the smallest circular column, etc. In addition, as in (C), regions other than the metal structures 205, the space 206 and a second metal 207 may be covered with a material 209 having a lower refractive index than the material that forms a substrate 204. Since unreacted fluorophores are unable to enter the regions covered with the low refractive index material 209, it is possible to reduce the background from these fluorophores.

Figure 3:
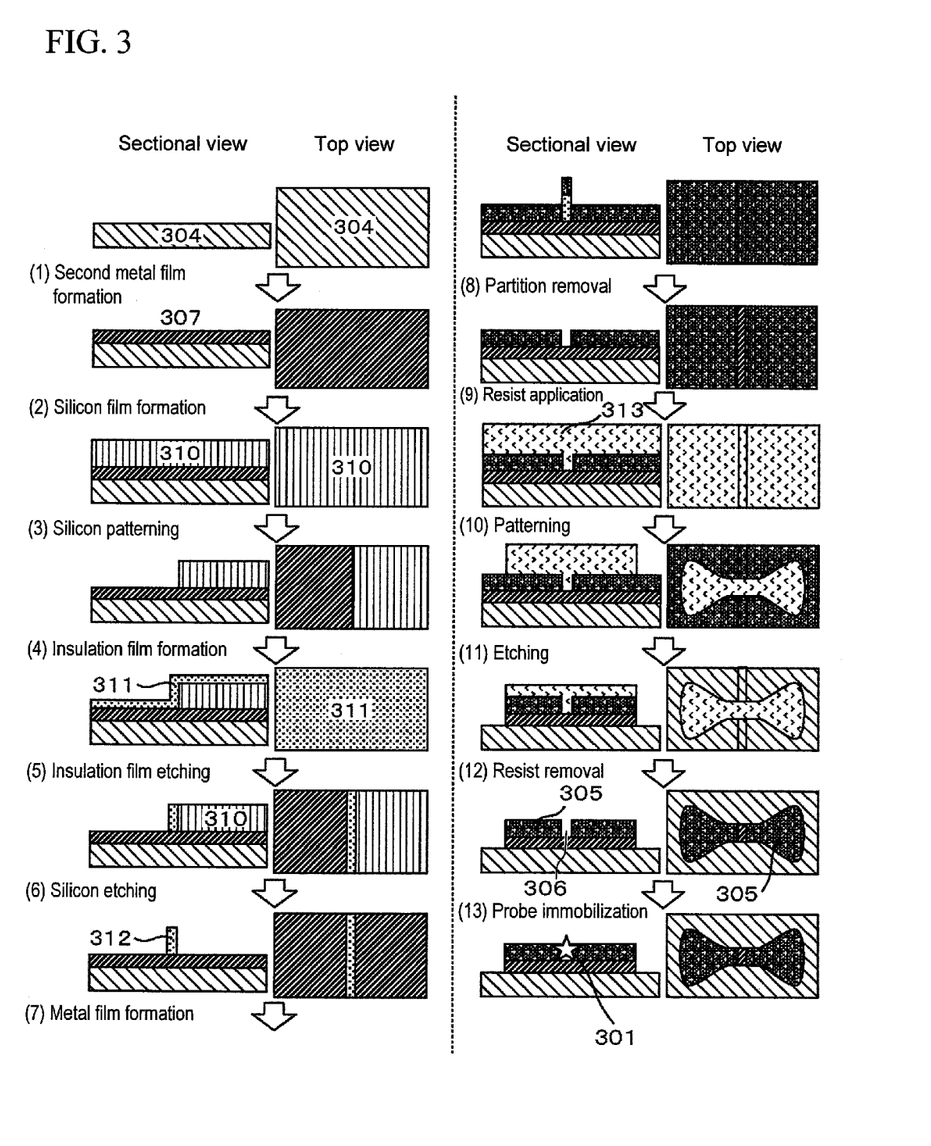
FIG. 3 is a flowchart illustrating an example of a method for producing a nucleic acid analyzing device.

A method for producing a nucleic acid analyzing device in which the probe is immobilized on the second metal is described with reference to FIG. 3.

(1) Second Metal Film Formation

A second metal 307 (thin film) is formed on a flat and smooth substrate 304. For the flat and smooth substrate 304, a glass substrate, a sapphire substrate, a resin substrate, etc., is used. If there is a need to deliver excitation light from the reverse side, which is on the opposite side to the side on which metal structures 305 are formed, a quartz substrate or a sapphire substrate with favorable optical transmissivity may be used. With respect to the second metal 307, when delivering the excitation light from the above-mentioned reverse side, it should preferably be thinner, and more preferably, it should be 5 to 100 nm. The thin film is produced using vapor deposition, sputtering, CVD, PVD, etc.

(2) Silicon Film Formation And (3) Silicon Patterning

A silicon film 310 is formed on the second metal 307 to be 5 nm or more in thickness. For the thin film formation method, vapor deposition, sputtering, CVD, PVD, etc., are preferable. Photolithography and etching are administered to the obtained silicon film 310 to perform patterning for creating a space 306 between the metal structures 305 where a localized surface plasmon is to be generated. The pattern conforms to a desired pattern for arranging the metal structures 305 facing each other in an array. For example, if the metal structures 305 are configured so as to face each other with a pitch of 1 μm, assuming that the formation region is 1 mm by 1 mm, then it would be possible to form one million reaction sites. For photolithography, there may be employed methods in which existing i-line (wavelength 365 nm), KrF excimer laser (wavelength 248 nm), ArF excimer laser (wavelength 193 nm), X-ray, or electron beam is adopted as a light source. In order to improve the patterning accuracy of etching, it is preferable that RIE (Reactive Ion Etching) be used.

(4) Insulation Film Formation, (5) Insulation Film Etching and (6) Silicon Etching An insulation film 311 is formed on silicon using CVD. The thickness of the insulation film 311 is for controlling the distance between the metal structures 305. The shorter the distance between the metal structures 305, the more the fluorescence intensifying effects of the localized surface plasmon can be enhanced. The preferred thickness is 50 nm or less, and should more preferably be 15 nm or less. As in the present embodiment of the invention, with a method that controls the distance between the metal structures 305 by way of the film thickness of the insulation film 311, even distances of 15 nm or less can be controlled accurately, and variations in production can be reduced. For such an insulation film, silicon dioxide and silicon nitride, which are used in fabrication processes for sidewalls (sidewall oxide films) of gate electrodes of semiconductors, are preferable. Although in the present embodiment of the invention there is presented a process that uses an insulation film, as long as it is possible to control the film thickness from the thin film formation process in (4) to the etching process in (6), it may also be implemented with a metal film. With respect to the etching used in these processes, RIE capable of fine processing is preferable.

(7) Metal Film Formation and (8) Partition Removal

The thickness of the metal film is for controlling the height of the metal structures 305. The thickness at which localized surface plasmons are generated effectively varies with the excitation wavelength used during measuring. The preferred thickness is 1,000 nm or less. For the thin film formation method, vapor deposition, sputtering, CVD, PVD, etc., may be used. To remove a partition 312, common wet (or dry) etching is performed. Specifically, for both silicon dioxide and silicon nitride, hydrofluoric acid or a solution containing hydrofluoric acid is used.

(9) Resist Application and (10) Patterning

The size and shape of the pattern are substantially related to the effects of the localized surface plasmon. In the case of a triangular shape such as that shown in FIG. 3, it is preferable that each side of the triangle be 1,000 nm or less. For a resist 313, a negative posist for electron beams may be used. Specifically, TEBN-1 (produced by Tokuyama Corporation) may be given as an example. After a resist is applied with a spinner, prebaking is performed with a hot plate for approximately two to five minutes. After writing with an electron beam with air acceleration voltage of 50 to 100 KV, development is carried out with ethyl lactate, isopropanol or ethanol.

(11) Etching and (12) Resist Removal

The metal structures 305 are formed with the patterned resist as a mask. For the purpose of improving patterning accuracy, RIE capable of fine processing is preferable. For resist removal, a widely used ozone ashing process may be used.

(13) Probe Immobilization

If the probe 101 is a nucleic acid, there are various conceivable methods for immobilization, as an example of which a method that employs aminosilane treatment will be discussed. The oxide film of the second metal 307 is treated with aminosilane to introduce an amino group. Then, after causing biotin-succinimide (NHS-Biotin produced by Pierce) to react, streptavidin is reacted. Next, by causing a probe that is terminally modified with biotin in advance to react, the probe is immobilized between the two metal structures 305 in close proximity to each other. Thus, the nucleic acid analyzing device is completed.

Even if the probe 101 were a protein like a nucleic acid synthetase, it can still be immobilized in a similar fashion. Specifically, by causing the nucleic acid synthetase to react after causing N-(4-Maleimidobutyryloxy) succinimide (GMBS produced by DOJINDO LABORATORIES), which is a bifunctional reagent, to react on an aminated oxide film, it is possible to immobilize the nucleic acid synthetase. In addition, it is also possible to use a method that utilizes physical adsorption with nitrocellulose, polyacrylamide, etc., on an oxide film, a method that utilizes the specific affinity between histidine and nickel ions or cobalt ions, or a method that utilizes binding between biotin and avidin, etc.

Figure 4:
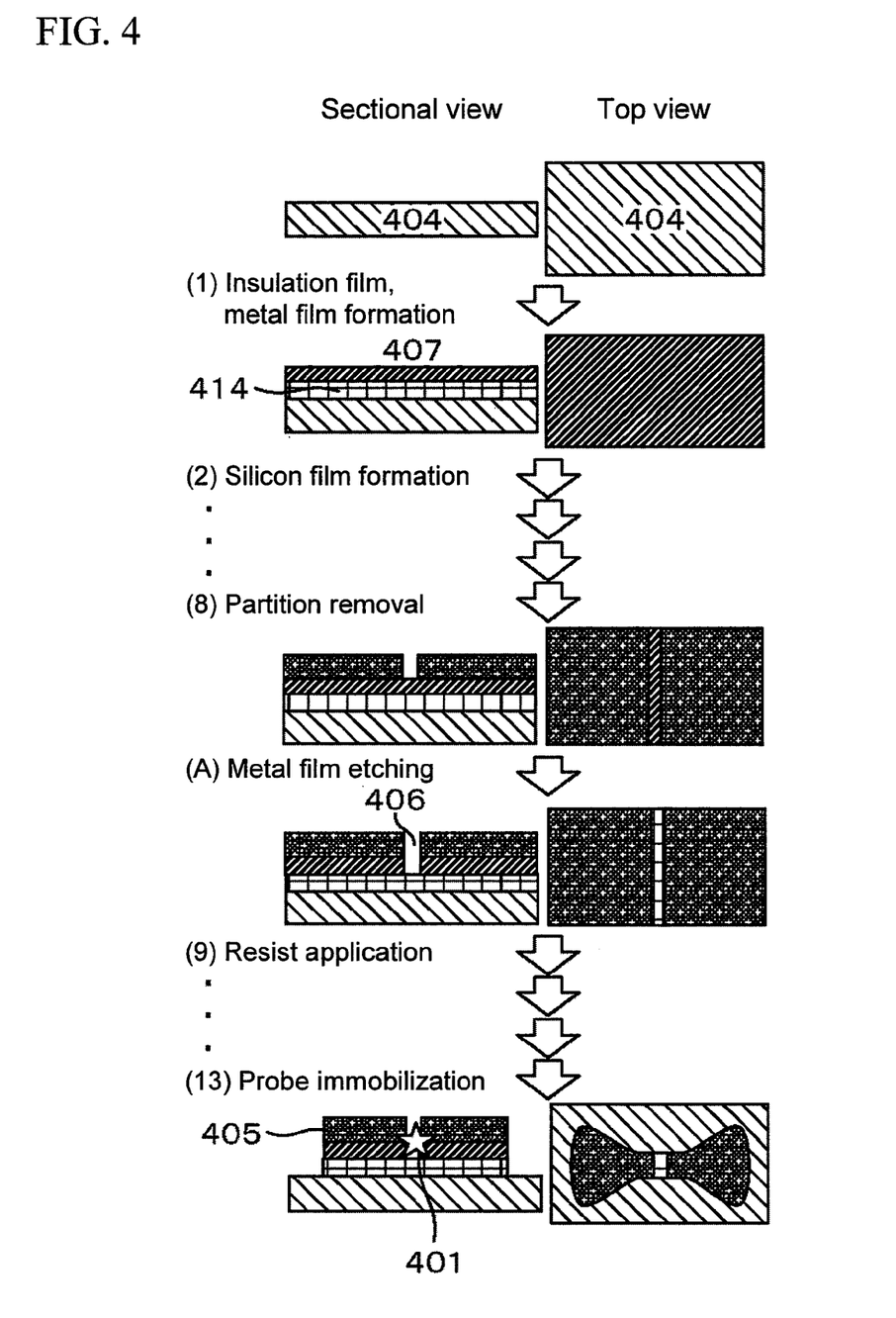
FIG. 4 is a flowchart illustrating an example of a method for producing a nucleic acid analyzing device.

A method for producing a nucleic acid analyzing device in which a probe is immobilized on an insulator will be described with reference to FIG. 4 mainly with respect to how it differs from FIG. 3.

(1) Insulation Film Formation

After an insulation film 414 is formed on a substrate 404 through vapor deposition, sputtering, CVD, PVD, etc., a metal film 407 is formed. The metal film 407 is for improving adhesion between the insulation film 414 and metal structures 405. For the insulation film 414, it is also possible to use an interlayer insulation film that can be formed with a spin coater (HSG produced by Hitachi Chemical Co., Ltd.), etc. The processes from (2) silicon film formation to (8) partition removal are similar to those in FIG. 3.

(A) Metal Film Etching

The metal film 407 is etched in order to expose the insulation film 414 at the interface with a space 406. The etching may be either of dry (and wet) etching, but for purposes of improving processing accuracy, RIE capable of fine processing is preferable. The processes from (9) resist application to (13) probe immobilization are performed in a similar fashion to those in FIG. 3.

Embodiment 2

Figure 5:
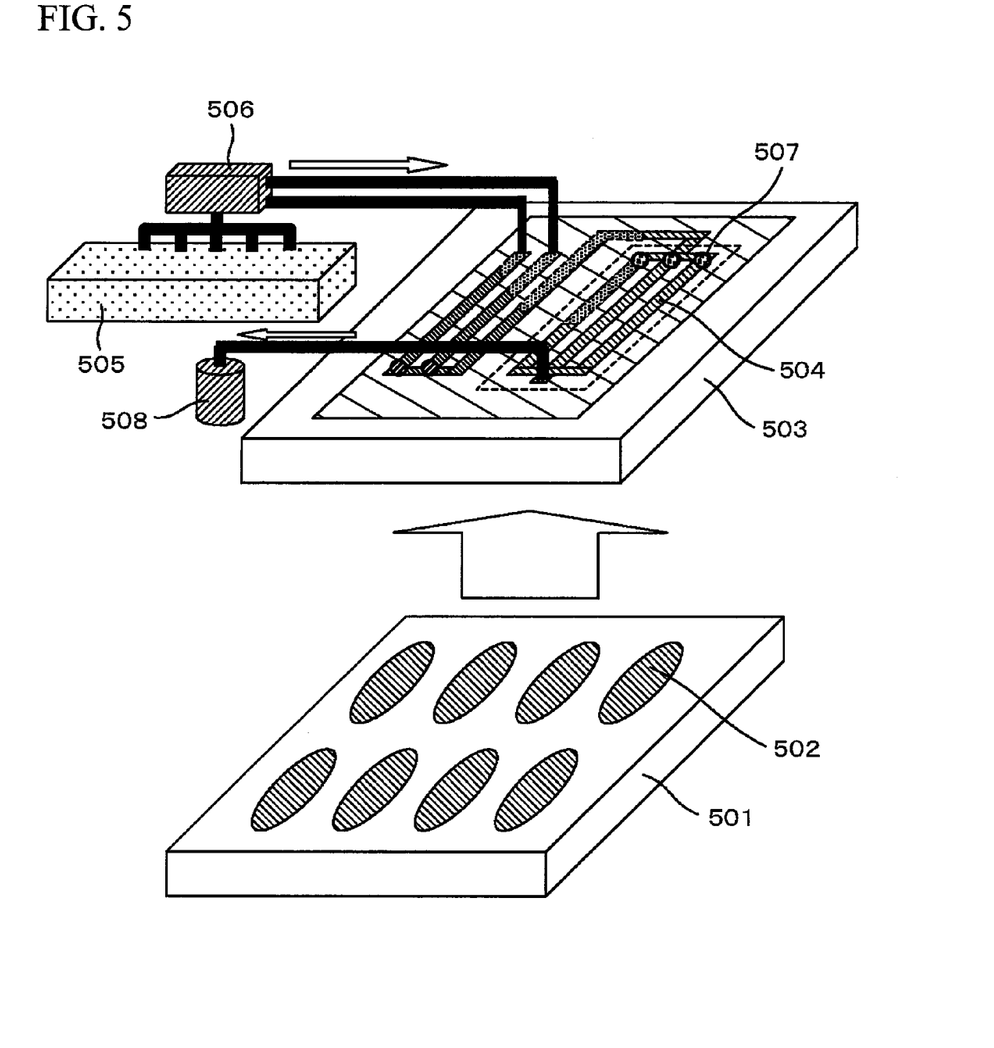
FIG. 5 is a schematic view illustrating an example of a mode of use for a nucleic acid analyzing device.

An example of a mode of use for a nucleic acid analyzing device will be described with reference to FIG. 5. A plurality of regions 502 in which metal structures are arranged in lattice form are mounted on a substrate 501. For the metal structures, the earlier-discussed structure applies where a probe is immobilized between two metal structures in close proximity to each other. The intervals for arrangement may be determined as deemed appropriate in accordance with the nucleic acid sample to be analyzed and the specifications of the fluorescence detection device. For example, if a 25 mm by 75 mm glass slide is used for the substrate 501, and the regions 502, in which the metal structures are arranged in lattice form at intervals of 1 micrometer, are 5 mm by 8 mm, it would then be possible to analyze 40 million kinds of nucleic acid molecules per region, and to mount approximately eight such regions on the substrate 501. Therefore, for example, when used in RNA expression analysis, since approximately 400,000 molecules of RNA are expressed per cell, it would be possible to perform RNA expression frequency analysis like digital counting with sufficient accuracy, and it would be possible to perform approximately eight analyses on a single substrate. As mentioned above, the provision of a plurality of reaction regions on the substrate 501 may be achieved by laying a reaction chamber 503, which is provided with passages 504 in advance, over the optically transmissive substrate 501. The reaction chamber 503 comprises a resin base body of PDMS (polydimethylsiloxane), etc., in which, for the formation of passages, grooves of the passages 504 are formed in advance, and is to be used by being adhered over the device. Specifically, it comprises: a temperature conditioning unit 505 that manages the temperature of and stores a nucleic acid sample, a reaction enzyme, a buffer, a nucleotide substrate, etc.; a dispensing unit 506 that delivers a reaction liquid; valves 507 that control the flow of liquid; and a waste liquid tank 508. As required, a temperature conditioner is provided and temperature control is effected. Upon completion of the reaction, a washing liquid is supplied via the passages 504 of the reaction chamber 503 and is received in the waste liquid tank 508.

Embodiment 3

Figure 6:
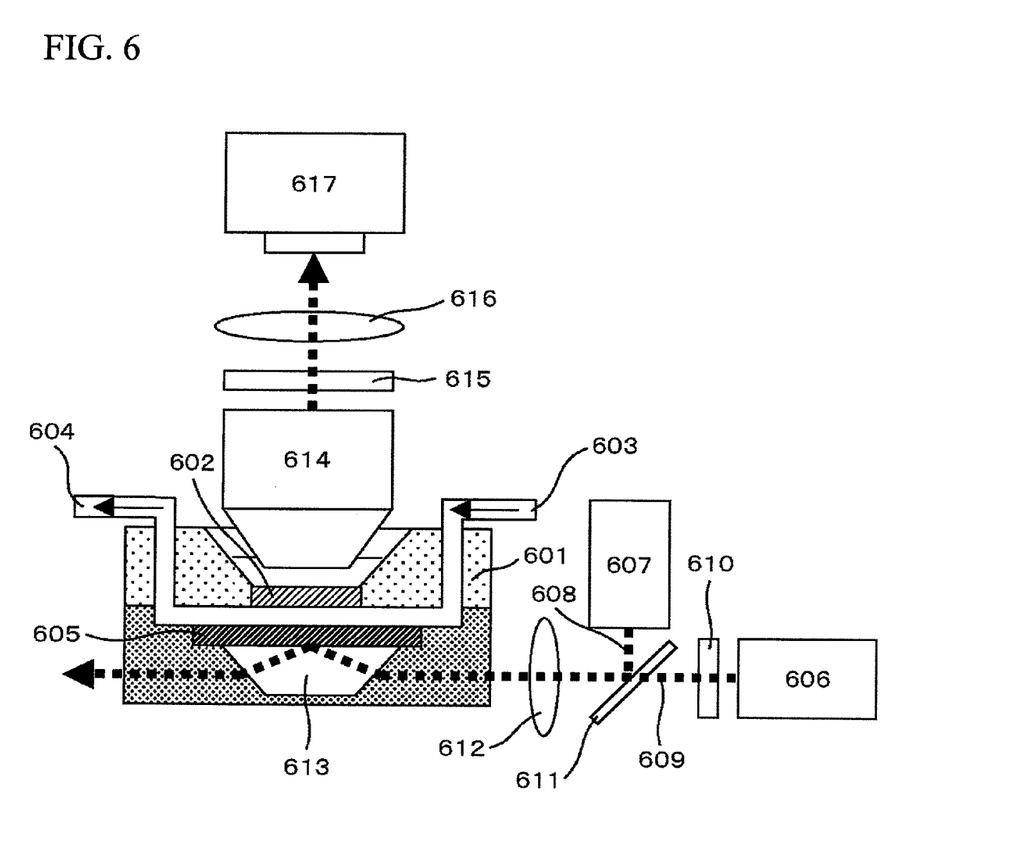
FIG. 6 is a schematic view illustrating an example of a nucleic acid analyzer that employs a nucleic acid analyzing device.

An embodiment of a nucleic acid analyzer will be described with reference to FIG. 6. The present embodiment of the invention comprises: a device that supplies to the nucleic acid analyzing device discussed above one or more kinds of biomolecules comprising a nucleotide, a nucleotide comprising a fluorophore, a nucleic acid synthetase, a primer, and a nucleic acid sample; a device that illuminates the nucleic acid analyzing device; and a fluorescence detection device that measures the fluorescence of a fluorophore that is incorporated into a nucleic acid strand due to a nucleic acid extension reaction that occurs by way of the coexistence of, on the nucleic acid analyzing device, the nucleotide, the nucleic acid synthetase, and the nucleic acid sample. More specifically, a nucleic acid analyzing device 605 with the structure discussed above is disposed in a reaction chamber comprising a cover plate 601, a detection window 602, and an inlet port 603 and outlet port 604, which are solution exchange ports. For the material of the cover plate 601 and the detection window 602, PDMS (polydimethylsiloxane) is used. Further, the detection window 602 is defined as being 0.17 mm in thickness. Laser beams 608 and 609 emitted from a YAG laser source (wavelength 532 nm, output 20 mW) 606 and a YAG laser source (wavelength 355 nm, output 20 mW) 607 are such that only the laser beam 609 is circularly polarized by a quarter-wave plate 610, and the two laser beams are so adjusted as to become coaxial by means of a dichroic mirror 611 (which reflects wavelengths of and below 410 nm), are thereafter focused by a lens 612, and are then cast upon the nucleic acid analyzing device 605 at the critical angle or greater via a prism 613. According to the present embodiment of the invention, localized surface plasmons are generated at the metal structures present on the surface of the nucleic acid analyzing device 605 by means of laser irradiation, and the fluorophores of the target substance captured by the probes bound to the second metal are thus present in the fluorescence intensifying field. The fluorophores are excited by the laser beams, and part of the intensified fluorescence is emitted via the detection window 602. In addition, the fluorescence emitted via the detection window 602 is turned into a collimated light beam by an objective lens 614 (×60, NA 1.35, operating distance 0.15 mm), and background light and the excitation light are blocked by an optical filter 615. An image is thus formed on a two-dimensional CCD camera 617 by an imaging lens 616.

In the case of a successive reaction scheme, one in which, as disclosed in P.N.A.S. 2006, vol. 103, pp. 19635-19640 (Non-Patent Document 6), as a fluorophore-attached nucleotide, a 3'—O-allyl group is incorporated at the 3'OH position on a ribose as a protective group, and in which a fluorophore is linked to the 5-position of the pyrimidines or the 7-position of the purines via an allyl group may be used. Since the allyl group is cleaved by illumination or through contact with palladium, it is possible to simultaneously attain dye quenching and control of the extension reaction. Even with successive reaction, there is no need to remove unreacted nucleotides by washing.

Further, with the present embodiment of the invention, since no washing step such as that disclosed in P.N.A.S. 2008, vol. 105, pp. 1176-1181 (Non-Patent Document 7) is required, it is possible to measure nucleic acid synthesis in real time. By thus building a nucleic acid analyzer using a nucleic acid analyzing device of an embodiment of the present invention, analysis time can be shortened and the device and the analyzer can be simplified without the inclusion of a washing step. It becomes possible to measure base nucleic acid synthesis in real time and not only by a successive reaction scheme, and a significant improvement in throughput over the prior art is thus possible.

DESCRIPTION OF SYMBOLS 101, 201, 301, 401 Probe
102 Fluorophore
103 Fluorophore of unreacted substrate
104, 204, 304, 404, 501 Substrate
105, 205, 305, 405 Metal suructures
106, 206, 306 Space in which localized surface plasmon is generated
107, 207, 307 Second metal
108 Nucleic acid
209 Low refractive index material
310 Silicon film
311 Insulation film
312 Partition
313 Resist
407 Metal film
414 Insulation film
502 Region in which metal structures are arranged in lattice form
503 Reaction chamber
504 Passage
505 Temperature conditioning unit
506 Dispensing unit
507 Valve
508 Waste liquid tank
601 Cover plate
602 Detection window
603 Inlet port
604 Outlet port
605 Nucleic acid analyzing device
606 YAG laser source (wavelength 532 nm, output 20 mW)
607 YAG laser source (wavelength 355 nm, output 20 mW)
608, 609 Laser beam
610 Quarter-wave plate
611 Dichroic mirror
612 Lens
613 Prism
614 Objective lens
615 Optical filter
616 Imaging lens
617 Two-dimensional CCD camera

The invention claimed is:

1. A nucleic acid analyzing device that analyzes a nucleic acid in a sample by luminescence, the nucleic acid analyzing device comprising:
a substrate;
a plurality of metal structures disposed on the substrate and facing each other, wherein a localized surface plasmon is generated by illumination in a space where the metal structures face each other;
a second metal that is different from the metal structures is provided between the space and the substrate so that the second metal is in contact with the space and a surface area of an upper surface of the second metal, which is in contact with the space, is smaller than a surface area of an upper surface of the plurality of metal structures; and
a single-molecule probe disposed on the second metal, wherein the probe is configured for analyzing the nucleic acid in the sample.

2. A nucleic acid analyzing device according to claim 1, wherein the plurality of metal structures comprise one or more kinds of metals selected from gold, silver, platinum, aluminum and copper.

3. A nucleic acid analyzing device according to claim 1, wherein the plurality of metal structures facing each other are arrayed on the substrate.

4. The nucleic acid analyzing device according to claim 1, wherein said space is 15 nm or less.

5. A nucleic acid analyzing method using the nucleic acid analyzing device according to claim 1, wherein
one or more kinds of biomolecules comprising a nucleotide comprising a fluorophore, a nucleic acid synthetase, a primer, and a nucleic acid sample are supplied to the nucleic acid analyzing device,
the nucleic acid analyzing device is illuminated to generate a localized surface plasmon in the space where the metal structures face each other,
fluorescence of a fluorophore, which is incorporated into a nucleic acid strand due to a nucleic acid synthesis, and the nucleic acid sample, is measured, and
a base sequence of the nucleic acid sample is analyzed.

6. A nucleic acid analyzing device that analyzes a nucleic acid in a sample by fluorescence, the nucleic acid analyzing device comprising:
a substrate;
a plurality of metal structures facing each other and separated by a space, wherein:
the plurality of metal structures comprises a first metal, and a localized surface plasmon is generated by illumination in said space where the metal structures face each other;
a second metal disposed on the substrate and in contact with and under the plurality of metal structures and said space, wherein the second metal is different than the first metal;
a surface area of an upper surface of the second metal which is in contact with the space is smaller than a surface area of an upper surface of the plurality of metal structures and
a single-molecule disposed on the second metal, wherein the probe is configured for analyzing the nucleic acid in the sample.

7. The nucleic acid analyzing device according to claim 6, wherein the metal structures comprise one or more kinds of metals selected from gold, silver, platinum, aluminum and copper.

8. The nucleic acid analyzing device according to claim 6, wherein the plurality of metal structures facing each other are arrayed on the substrate.

9. The nucleic acid analyzing device according to claim 6, wherein said space is 15 nm or less.

* * * * *